United States Patent [19]

Kashibuchi et al.

[11] Patent Number: 5,565,207

[45] Date of Patent: Oct. 15, 1996

[54] SCALP MOISTURIZER AND EXTERNAL SKIN PREPARATION

[75] Inventors: Nobuo Kashibuchi; Kenkichi Matsubara; Yoshio Kitada; Hiroyuki Suzuki, all of Kanagawa-ken, Japan

[73] Assignee: Pola Kasei Kogyo Kabushiki Kaisha, Shizuoka-ken, Japan

[21] Appl. No.: 311,448

[22] Filed: Sep. 26, 1994

Related U.S. Application Data

[63] Continuation of Ser. No. 990,238, Dec. 14, 1992, abandoned, which is a continuation-in-part of Ser. No. 755,134, Sep. 5, 1991, abandoned.

[30] Foreign Application Priority Data

Sep. 19, 1990 [JP] Japan .................................. 2-247157
Jul. 18, 1991 [JP] Japan .................................. 3-268135

[51] Int. Cl.⁶ ........................................................ A61K 7/00
[52] U.S. Cl. .......................... 424/401; 424/74; 514/352; 514/880; 514/881
[58] Field of Search .............................. 424/401, 47, 74, 424/195.1; 514/880, 881, 874, 852, 179, 844

[56] References Cited

U.S. PATENT DOCUMENTS

| | | | |
|---|---|---|---|
| 4,278,657 | 7/1981 | Tezuka et al. | 424/63 |
| 4,686,211 | 8/1987 | Hara et al. | 514/148 |
| 4,950,481 | 8/1990 | Keri et al. | 424/195.1 |
| 5,124,081 | 6/1992 | Vanlerberghe et al. | 424/450 |

FOREIGN PATENT DOCUMENTS

| | | |
|---|---|---|
| 61-289013 | 12/1986 | Japan . |
| 62-072604 | 4/1987 | Japan . |
| 62-187404 | 8/1987 | Japan . |
| 63-192703 | 8/1988 | Japan . |
| 1-040412 | 2/1989 | Japan . |
| 2-006403 | 1/1990 | Japan . |

OTHER PUBLICATIONS

The Merck Manual, 15th Ed. Berkow et al, pp. 2247–2253, 2258, 2259 (1987).
Keshohin–Kagaku Guidebook (The Society of Cosmetic Chemists of Japan, pp. 152–153.
Holzle et al (1977) The Journal of Investigative Dermatology 68:350–56.
Nikko Handbook, pp. 298–313.
Grove et al (1983) in Marks et al eds., Stratum Corneum, Springer–Verlag, NY pp. 191–195.

*Primary Examiner*—John C. Bleutoe
*Assistant Examiner*—Robert H. Harrison
*Attorney, Agent, or Firm*—Birch, Stewart, Kolasch & Birch, LLP

[57] ABSTRACT

A scalp-moisturizer or external skin preparation containing as essential active ingredients the following: (a) steroid glycoside and/or triterpenoid glycoside, (b) sphingo glycolipid and (c) steroid hormone, the content of (a) and (b) being 0.01–10% by weight of the total, the (a)/(b) ratio by weight being 85/15–30/70 and (c) being incorporated in effective amounts of not more than 0.1% by weight of the total.

14 Claims, 4 Drawing Sheets

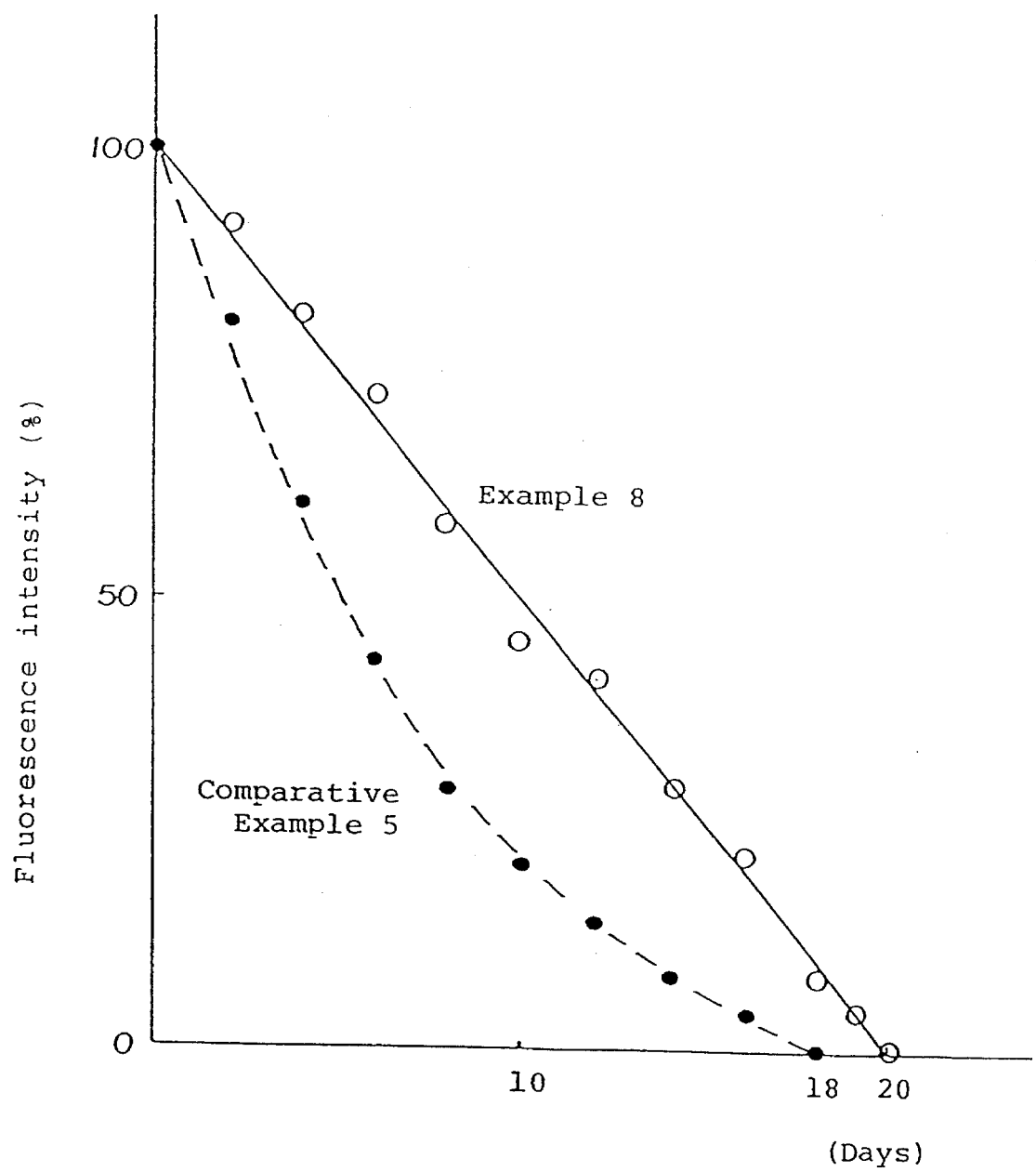

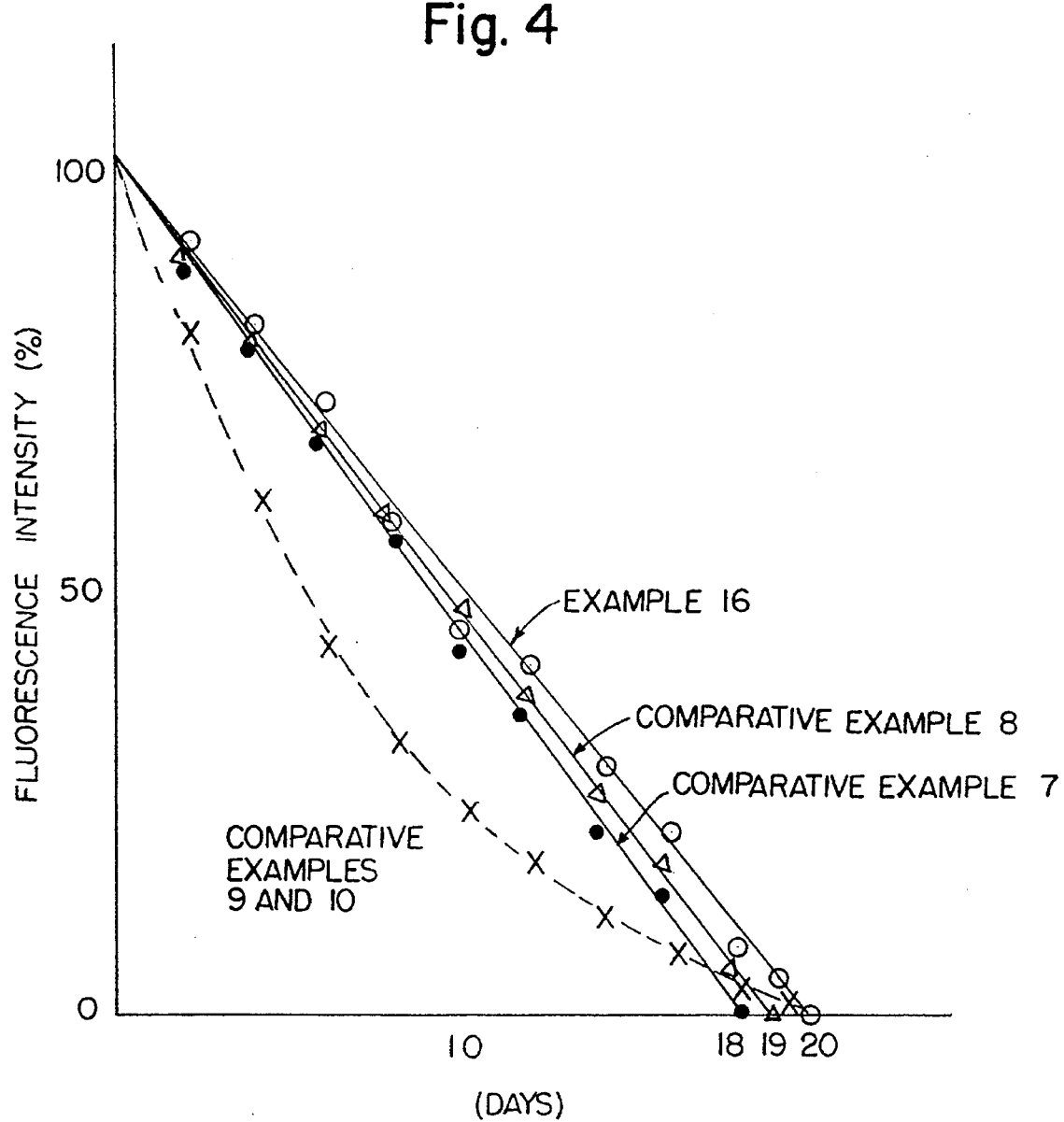

SCALP MOISTURIZER AND EXTERNAL SKIN PREPARATION

This application is a continuation of application Ser. No. 07/990,238 filed on Dec. 14, 1992, now abandoned, which is a continuation-in-part of application Ser. No. 07/755,134, filed on Sep. 5, 1991, now abandoned.

FIELD OF THE INVENTION

This invention relates first of all to a scalp moisturizer. More particularly it is directed to a scalp moisturizer of new formulation having incorporated therein those glycosides, glycolipids etc. which are excellent in the effects of suppressing dandruff production in the scalp and providing the hair with moisture.

The present invention further relates to an external skin preparation. More particularly it provides an external skin preparation having such an action as to normalize the skin physiology and thereby recover the regularity of cellular arrangement of corneocytes through the normalization and retardation of the turnover of the stratum corneum, and thus showing an action of improving skin-roughening.

Scalp moisturizers are believed to have different effects such as impartation of aroma and refreshing feel to the scalp or hair and action on the hair root, or on the skin as such, to accelerate the hair growth or to suppress dandruff production or itching. The major cause for the production of dandruff and itching is considered to be the abnormal desquamation and sebum secretion acceleration, and growth of microorganisms is pointed out to be an aggravating factor (see, for example, Keshohin-Kagaku Guidebook, edited by Nippon Keshohin Gijutsusha Kai, Yakuji Nipposha Co., Ltd. p. 152).

Heretofore, shampoos having incorporated therein different sulfur-containing compounds with antibacterial activity have frequently been used for removal of dandruff. Also commercially available for the same purpose are tonic agents wherein in addition to antibacterials various vitamins or anti-histaminics such as diphenylhydrazine hydrochloride are incorporated in different appropriate combinations as scalp moisturizers/hair growth accelerator (see, for example, Hifu To Biyo, 9[2] p. 1371 (1977)). For the purpose of providing the hair with moisture, on the other hand, hair rinses are in use which contain cationic surfactants or humectants as active ingredients.

The performance of such products now put on the market have both advantages and disadvantages, and they are unsatisfactory for use as scalp moisturizers. Further, little has been known as to scalp moisturizers, based on their action on the scalp to normalize its physiology.

Furthermore, according to the present invention, there is provided a novel external skin preparation. Prior art external skin preparations which claim to be effective in improving skin-roughening base their effect, in the majority of cases, on the action of retaining moisture in the skin. The retaining of the skin moisture can be effected either by suppressing transepidermal water loss (T.W.L.) with blocking agents or by enhancing the skin hydration effect with humectants.

The former method utilizes vaseline-based ointments or water-in-oil type emulsions as substances or materials of high coherence with the skin and hydrophobicity. Such substances or materials, however, are associated with drawbacks of giving an unpleasant, e.g. oily or greasy, sense of touch.

The latter method employs emulsified compositions containing humectants of excellent hygroscopic and humectic capacity as typified by polyhydric alcohols such as sorbitol, maltitol, ethylene glycol, propylene glycol, 1,3-butylene glycol or glycerin, urea or salts of organic acids such as sodium pyrrolidonecarboxylate or sodium lactate. This method has the drawback that if the effect is to be enhanced large amounts of these substances have to be incorporated with the result that an unpleasant, e.g., greasy or slimy, sense of touch is produced.

Furthermore, neither method is able to recover the regularity of cellular arrangement of corneocytes.

In Japanese Laid open Patent Appln. Sho. 62-187404 (Unexamined Patent Application Publication No. 187404/87) is described that cosmetics having incorporated therein specific amounts of sphingo glycolipid and steroid glycoside and/or triterpenoid glycoside are excellent in the function of retaining moisture. With these cosmetics, the turnover of the stratum corneum can be normalized but the recovery of the regularity of cellular arrangement of corneocytes cannot be expected.

In E. Hölzle & G. Plewig, J. Invest. Dermatol., 68, 350 (1977) is disclosed that when adrenocortical hormones were topically applied to the skin and observed for changes in the morphology of corneocytes they were found in particular to contribute to the retardation of their turnover. No clear reference, however, is made as to the recovery of the regularity of the cellular arrangement of corneocytes.

Nikko Handbook (published by Nikko Chemicals Co., Ltd.) describes that estrogen (follicular hormone) inhibits dermal growth. Nothing, however, is described therein as to recovery of the regularity of the cellular arrangement of corneocytes.

SUMMARY OF THE INVENTION

An object of the present invention is to provide a scalp moisturizer which exhibits the effects of suppressing dandruff formation in the scalp and providing the hair with moisture, through the normalization and retardation, as a result of the scalp physiology being normalized, of the turnover of scalp stratum corneum, to recover the regularity of the cellular arrangement of corneocytes and improve multi-layer desquamation.

As a result of their extensive research to explore a scalp moisturizer having a high dandruff-suppressive effect, the present inventors have found those substances which are effective in recovering the regularity of the cellular arrangement of scalp corneocytes and improving multi-layer desquamation.

Thus, according to the present invention, there is provided a scalp moisturizer which comprises (a) steroid glycoside and/or triterpenoid glycoside, (b) sphingo glycolipid and (c) steroid hormone, the content of (a) and (b) being 0.01–10% by weight of the total, the (a)/(b) ratio by weight being 85/15–30/70 and (c) being incorporated in effective amounts of not more than 0.1% by weight of the total. There is further provided, as a preferred embodiment, a scalp moisturizer which contains, in addition to the ingredients mentioned above, one or more of sebum secretion inhibitors and/or potent antibacterials against the microbe *Pityrosporum ovale*.

Another object of the present invention is to provide an external skin preparation which exhibits the effect of improving skin-roughening, as a result of the scalp physiology being normalized through the normalization and retardation of the of the stratum corneum, to recover the regularity of the cellular arrangement of corneocytes and to improve multi-layer desquamation.

As a result of their extensive research on the recovery of the regularity of cellular arrangement of skin corneocytes, the present inventors have succeeded in developing an external skin preparation which exhibits a remarkable effect of improving skin-roughening. Thus, according to the present invention, there is provided an external skin preparation which comprises (a) steroid glycoside and/or triterpenoid glycoside, (b) sphingo glycolipid and (c) steroid hormone, the content of (a) and (b) being 0.01–10% by weight of the total, the (a) /(b) ratio by weight being 85/15–30/70 and (c) being incorporated in effective amounts of not more than 0.1% by weight of the total. There is further provided, as a preferred embodiment, an external skin preparation which contains, in addition to the ingredients mentioned above, one or more of an anti-inflammatory agent, cell activator, peroxidized lipid formation inhibitor and humectant.

BRIEF DESCRIPTION OF THE DRAWINGS

FIGS. 1–4 are graphs showing the results of comparative measurements of the normalization and retardation of stratum corneum turnover with an example of the external skin preparation of the present invention and comparative examples of external skin preparations.

DETAILED DESCRIPTION OF THE INVENTION

Figure 1:
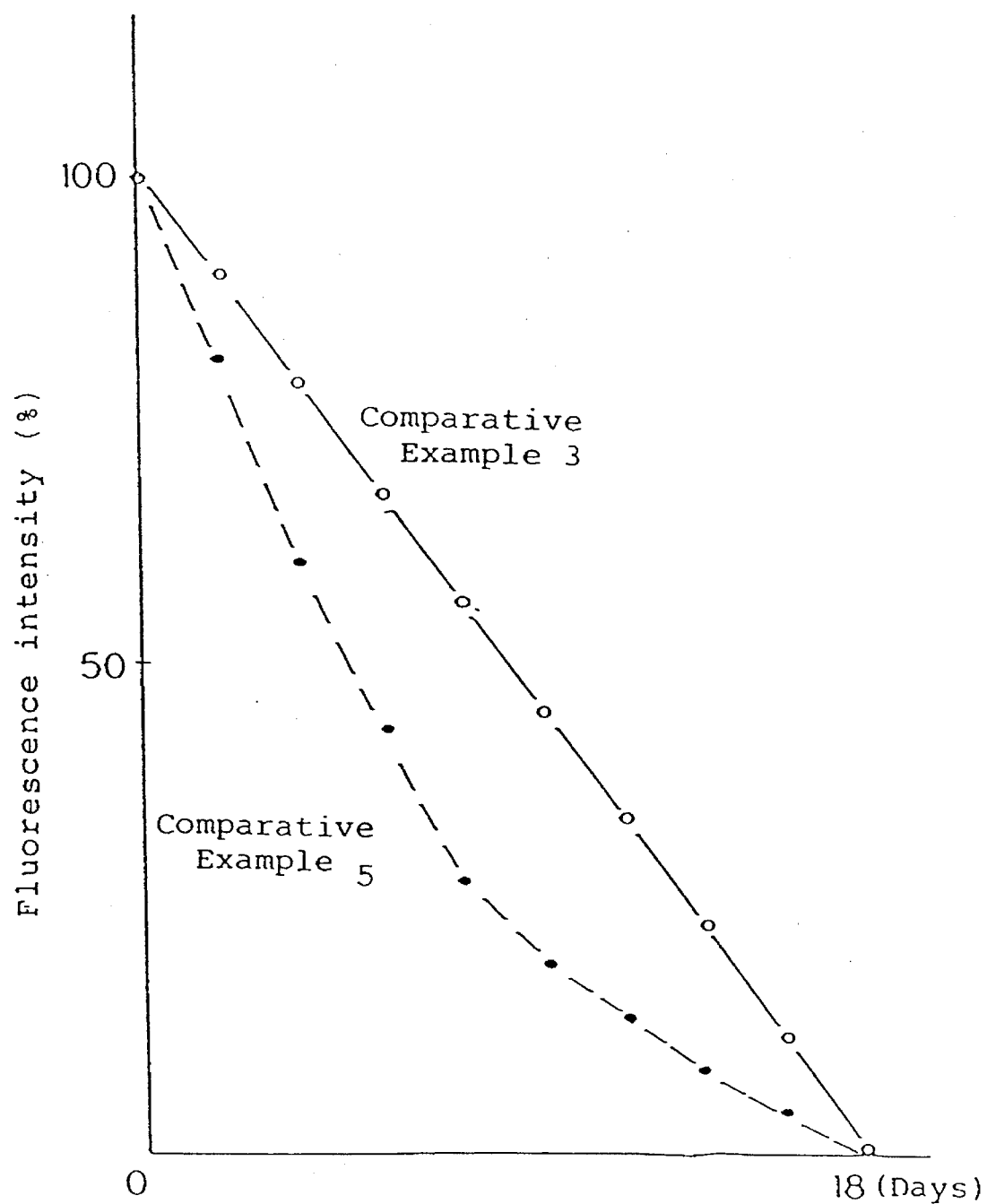

The present invention will now be described in detail in the following.

Examples of the steroid glycoside mentioned above for use in the scalp moisturizer or external skin preparation of the present invention include campesterol glycoside, stigmasterol glycoside, β-sitosterol glycoside, cholesterol glycoside, stigmastenol glycoside and avenasterol glycoside.

Examples of the triterpenoid glycoside mentioned above for use in the scalp moisturizer or the external skin preparation of the present invention include cycloartenol glycoside, 24-methylenecycloartenol glycoside, cycloartanol glycoside, cyclobranol glycoside, glycyrrhizin and ginsenoside.

The sphingo glycolipids mentioned above for use in the scalp moisturizer or external skin preparation of the present invention are a class of glycolipids, i.e. substances containing both fatty acid and glucide in the molecule, which have therein the sphingosine skeleton as represented by dihydrosphingosine, sphingosine, phytosphingosine, dehydrophytosphingosine etc. Examples of the sphingo glycolipid include monohexosylceramide (cerebroside), sphingoplasmalogen, monohexosylceramide fatty acid ester (cerebroside ester) such as galactosylceramide fatty acid ester or glycosylceramide fatty acid ester, dihexosylceramide Such as D-galactosyl (1→4)D-glycosyl (1→) ceramide or D-galactosyl (1→4)D-galactosyl (1→) ceramide, trihexosylceramide such as D-galactosyl (1→4)D-galactosyl (1→4)D-glucosyl (1→) ceramide, galactosyl-ceramide sulfate (cerebroside sulfate, i.e. sulfatide), dihexosyl-ceramide sulfate, globoside such as N-acetylgalactosamine ( 1→3)D-galactosyl (1→4)D-galactosyl (1→4)D-glucosyl (1→)ceramide [globoside I], N-acetylgalactosamine-( 1→4)D-galactosyl (1→4)D-glucosyl (1→) ceramide, D-galactosyl (1→3)N-acetylgalactosamine (1→4)D-galactosyl (1→4)glycosyl (1→) ceramide or D-galactosyl (1→3)D-galactosyl (1→3)N-acetylglucosamine (1→3)D-galactosyl (1→4)D-glucosyl (1→)ceramide, hematoside such as N-acetylneuraminic acid (2→3)D-galactiosyl (1→4)D-glucosyl (1→)ceramide or N-acetylneuraminic acid (2→3)D-galactosyl (1→) ceramide, and ganglioside containing both sialic acid and hexosamine in addition to neutral glucide.

In incorporating steroid glycoside and/or triterpenoid glycoside and sphingo glycolipid into the scalp moisturizer or external skin preparation of the present invention, each of the components may be incorporated as appropriate upon preparation of the scalp moisturizer or external skin preparation. In order to enhance the effects of the scalp moisturizer or external skin preparation, it is preferable first to heat steroid glycoside and/or triterpenoid glycoside and sphingo glycolipid in the presence of an appropriate organic solvent and then to distill off the solvent from the resultant solution to afford an integrated product which is then added to an oil phase prior to use.

Steroid glycoside, triterpenoid glycoside and sphingo glycolipid are all contained in natural materials widely occuring in the animal and plant kingdoms. Therefore, from the industrial perspective, it is most preferable to use extracts as such obtained from these natural materials using organic solvents. In such cases, however, the content of steroid glycoside, triterpenoid glycoside and sphingo glycolipid will be dependent upon the species, part etc. of the plant or animal used as raw materials. It follows that the choice of raw materials is important since the ratio in the resultant extract of (steroid glycoside+triterpenoid glycoside)/sphingo glycolipid is an important element of the present invention.

Examples of materials which meet the conditions in respect of the ratio mentioned above include rice bran, wheat bran (wheat embryo bud), millet, barnyard grass, soybean, kaoliang and corn, and these materials can be preferably used as raw materials for the scalp moisturizer or external skin preparation of the present invention.

In extracting mixtures of steroid glycoside and/or triterpenoid glycoside and sphingo glycolipid from these plant materials, any appropriate procedure may be employed. For example, the raw materials may be subjected, after being pretreated if necessary, to extraction with organic solvents such as chloroform, methanol, butanol or isopropanol, used alone or as mixtures, followed by separation and recovery, for example by way of column chromatography.

In the scalp moisturizer or external skin preparation, there are incorporated one or more ingredients selected from steroid glycosides and triterpenoid glycosides, and one or more ingredients selected from a class of sphingo glycolipids, in amounts of 0.01–10% preferably 0.5–2.0% by weight based on the total weight of the composition.

The (a) steroid glycoside and/or triterpenoid glycoside/(b) sphingo glycolipid ratio by weight is 85/15–30/70. With larger amounts of (a) beyond this range, its solubility in bases for the scalp moisturizer or external skin preparation becomes lower. As a result of this no satisfactory effect of dandruff suppression can be achieved with the so obtained scalp moisturizer and also no satisfactory effect of improving skin-roughening with the so obtained external skin preparation. With lesser amounts of (a) below the range, no satisfactory effect of dandruff suppression can be achieved with the so obtained scalp moisturizer and also no satisfactory effect of improving skin-roughening with the so obtained external skin preparation. As the most preferable range there may be mentioned 60/40–85/15.

In the following will now be shown some examples of preparation where mixtures of the steroid glycoside, triterpenoid glycoside and sphingo glycolipid mentioned above are obtained from plant materials by extraction with organic solvents.

Preparation 1

As a pretreatment, wheat bran was extracted with hexane and the resultant oil was treated with sulfuric acid to obtain a precipitate. The thus formed precipitate (100 g) was treated with a mixed solvent (1 l) of chloroform/methanol (=1/1) and the solids were filtered off. The filtrate was concentrated under reduced pressure and methanol (200 ml) was added to the resultant concentrate for redissolution. Insolubles were filtered off and the filtrate was applied on a silica gel column chromatography. As eluting solvents, chloroform/methanol (=95/5) was first used to elute neutral lipid, cholesterol, fatty acid etc. and chloroform/methanol (=75/25) then used to elute a mixture of sphingo glycolipid, steroid glycoside and triterpenoid glycoside. Yield 0.7 g. Component ratio of mixture:

(Steroid glycoside+triterpenoid glycoside)/sphingo glycolipid=80/20

Preparation 2

As a pretreatment, rice bran was extracted with hexane, and the resultant oil was treated with sulfuric acid to obtain a precipitate. The thus formed precipitate (100 g) was treated with a mixed solvent (1 l) of chloroform/methanol (=2/1) and the solids were filtered off. The filtrate was concentrated under reduced pressure and chloroform (100 ml) was added to the resultant concentrate for redissolution. The solution was a applied on a silica gel column chromatography. As eluting solvents, chloroform/methanol (=9/1) was first use, J to elute neutral lipid, cholesterol, fatty acid etc. and chloroform/methanol (=8/2) then used to elute a mixture of the desired sphingo glycolipid, steroid glycoside and triterpenoid glycoside. Yield 1 g. Results of T.L.C. analysis (developing solvent: benzene/ethanol=5/1)

| Rf values | 0.25–0.28 | (sphingo glycolipid) |
|---|---|---|
| | 0.32–0.35 | (steroid glycoside + triterpenoid glycoside) |

Component ratio of mixture:
(Steroid glycoside + triterpenoid glycoside)/
Sphingo glycolipid = 70/30)

As steroid hormones suitable for use in the scalp moisturizer or external skin preparation may be mentioned follicular hormones and adrenocortical hormones. Examples of follicular hormones include estradiol and its esters, estrone and ethynylestradiol, and those of adrenocortical hormones include cortisone and its esters, hydrocortisone and its esters, prednisone and predenisolone. Any commercially available products of these steroid hormones may be used as such or after further processing.

In the scalp moisturizer or external skin preparation of the present invention are incorporated one or more of the steroid hormones mentioned above in effective amounts not more than 0 1% preferably in the range of 0.001–0.1% by weight of the total.

The scalp moisturizer according to the present invention may contain additional active ingredients other than the essential active ingredients mentioned above. A preferred example of such ingredient is sebum secretion inhibitor. Examples of sebum secretion inhibitor include pantetheine, vitamin $B_6$, anti-androgenics and organic solvent extracts of ginseng, Citrus Unshiu or Houthuyniae Herba.

Likewise as potent antibacterials against the microbe *Pityrosporum ovale* to be incorporated into preferred embodiments of the scalp moisturizer of the present invention may be used any known such materials as such or in further processed forms. Examples of such antibacterials include sulfur, sulfur compounds such as cadmium sulfide or zinc pyridinium-1-thiol-N-oxide (Zpt), triclosan, halocarban, menthols, undecylenic acid, resorcin, isopropylmethylphenol and salicylic acid.

Other ingredients which may be incorporated into the scalp moisturizer in accordance with the present invention include those which are customarily used in scalp moisturizers, for example hydrocarbons, waxes, fats and oils, esters, higher fatty acids, higher alcohols, surfactants, perfumes, coloring matters, antioxidants, sunscreening agents, alcohols and buffer solutions for pH adjustment.

Furthermore, other active ingredients of different types may be incorporated into the scalp moisturizer of the present invention in accordance with its particular use, for example, anti-inflammatory agents such as glycyrrhizic acid or bisabolol, 1-methyl-4-(1-hydroxyl-1,5,5-trimethyl-4-pentenyl-)cyclohex-1-ene, cell activators such as allantoin or placental extracts, peroxidized lipid formation inhibitors such as vitamin E or superoxide dismutase (SOD), humectants such as sodium hyaluronate or blood circulation accelerators such as vitamin E nicotinate.

The external skin preparation according to the present invention may contain additional active ingredients other than the essential active ingredients mentioned above. Examples of anti-inflammatory agents which is one of such additional ingredients include glycyrrhezic acid or its derivatives, glycyrrhizic acid or its derivatives, bisabolol, 1-methyl-4-(1-hydroxyl-1,5,5-trimethyl-4-pentenyl)cyclohex-1-ene and extracts from geranii herba, horse chestnut, Japanese Angelica or aloe.

Likewise, as examples of cell activators which are to be incorporated into preferred embodiments of the external skin preparation of the present invention may be mentioned allantoin or its derivatives, or extracts from biological materials such as Japanese Angelica, rosemary or placentas.

Likewise, as examples of peroxidized lipid formation inhibitor which may be incorporated may be mentioned vitamin E, superoxide dismutase (SOD) and tannins.

Likewise, as examples of humectant which may be incorporated may be mentioned sodium hyaluronate and collagen.

Other ingredients which may be incorporated into the external skin preparation of the present invention are those which are customarily used in topical skin agents, for example hydrocarbons, waxes, fats and oils, esters, higher fatty acids, preservatives, antioxidants, sunscreening agents, alcohols and higher alcohols, surfactants, perfumes, coloring matters, buffer solutions for pH adjustment. Further active ingredients of different types may also be incorporated in accordance with the particular use of the external skin preparation of the present invention.

The scalp moisturizer of the present invention may take different forms, for example, scalp essences, shampoos or tonics.

The external skin preparation of the present invention may also take different forms, for example, creams, emollient lotions, moisturizing lotions, gels or ointments.

In the following will now be described the present invention in more detail with reference to examples of the present invention as well as comparative examples for the purpose of comparison. It is to be understood that the present invention be by no means limited by these examples. The numerical values for amounts incorporated are in parts by weight.

[Scalp Moisturizer]

Examples 1–7 and 15 and Comparative Examples 1–2 and 6 relate to scalp moisturizer.

Examples 1–4 and Comparative Example 1

Scalp essence is prepared.
Formulation is shown in Table 1.

TABLE 1

Formulation of Scalp Essence

| | Raw materials | Example 1 | 2 | 3 | 4 | Comparative Example 1 |
|---|---|---|---|---|---|---|
| (1) | Squalane | 3.0 | 3.0 | 3.0 | 3.0 | 3.0 |
| | Methylpolysiloxane | 0.3 | 0.3 | 0.3 | 0.3 | 0.3 |
| | Propyl para-hydroxybenzoate | 0.05 | 0.05 | 0.05 | 0.05 | 0.05 |
| | Polyoxyetylene behenyl ether (20 E.O.) | 1.5 | 1.5 | 1.5 | 1.5 | 1.5 |
| | Sorbitan monostearate | 0.7 | 0.7 | 0.7 | 0.7 | 0.7 |
| | Product from Preparation 2 | 2.0 | 2.0 | 2.0 | 2.0 | — |
| (2) | Xantane gum | 0.3 | 0.3 | 0.3 | 0.3 | 0.3 |
| | Methyl para-hydroxybenzoate | 0.3 | 0.3 | 0.3 | 0.3 | 0.3 |
| | Glycerin | 15.0 | 15.0 | 15.0 | 15.0 | 15.0 |
| | Purified water | 76.749 | 76.74 | 76.72 | 76.62 | 78.75 |
| (3) | Estrone | 0.001 | 0.01 | 0.01 | 0.01 | — |
| | Resorcin | — | — | 0.02 | 0.02 | — |
| | Pantethine | — | — | — | 0.1 | — |
| | Perfume | 0.1 | 0.1 | 0.1 | 0.1 | 0.1 |

Method of Preparation

By heating at 80° C. raw materials indicated in (1) in Table 1 and those indicated in (2), respectively, to obtain the solution from (1) and the solution (2). A part of the solution from (2), is slowly added with stirring to the solution from (1) and after reversal emulsification the remainder of the solution from (2) is added. The mixture is cooled down to 40° C. with stirring and after addition of the raw materials indicated in (3) in Table 1 further down to 30° C.

Example 15 and Comparative Example 6

Scalp essence is prepared.
Formulation is shown in Table 12.

TABLE 12

Formulation of Scalp Essence

| | Raw materials | Example 15 | Comparative Example 6 |
|---|---|---|---|
| (1) | Squalane | 3.0 | 3.0 |
| | Methylpolysiloxane | 0.3 | 0.3 |
| | Propyl para-hydroxybenzoate | 0.05 | 0.05 |
| | Polyoxyethylene behenyl ether (20 E.O.) | 1.5 | 1.5 |
| | Sorbitan monostearate | 0.7 | 0.7 |
| | Steroid glycoside and | 1.0 | 0 |

TABLE 12-continued

Formulation of Scalp Essence

| | Raw materials | Example 15 | Comparative Example 6 |
|---|---|---|---|
| | triterpenoid glycoside Sphingo glycolipid | 1.0 | 0 |
| (2) | Xantane gum | 0.3 | 0.3 |
| | Methyl para-hydroxybenzoate | 0.3 | 0.3 |
| | Glycerin | 15.0 | 15.0 |
| | Purified water | 76.73 | 78.73 |
| (3) | Hydrocortisone | 0.02 | 0.02 |
| | Perfume | 0.1 | 0.1 |

Method of Preparation

The raw materials indicated in (1) in Table 12 and those indicated in (2) in Table 12 shown above are separately dissolved by heating them at 80° C. A part of the solution from (2) is slowly added with stirring to the solution from (1) and after reversal emulsification the remainder of the solution from (2) is added. The mixture is cooled down to 40° C. and after addition of the raw materials in (3) further down to 30° C.

Results of the following tests A, B and C are shown which were carried out with the scalp essences formulated in accordance with Examples 1–4 and 15 and Comparative Examples 1 and 6 shown above and those of test A are also shown which was carried with the scalp essences formulated in accordance with Example 15 and Comparative Example 6:

A: Test for the recovery of regularity of cellular arrangement of scalp corneocytes and for the improvement in multi-layer desquamation B: Visual observation of scalp lesions C: Test for hair moisturizing effect A. Test for the recovery of regularity of cellular arrangement of scalp corneocytes and for the improvement in multi-layer desquamation Samples Scalp essences from Examples 1–4 and 15 and Comparative Examples 1 and 6

Procedure (1) Healthy male subjects to be tested in their twenties to forties have their hair cut with a hair-cutter and then get their head shaved with a shaver. There are used fifteen for Examples 1–4 and Comparative Example 1 and ten such subjects for Example 15 and Comparative Example 6. A 24-hours closed patch test is carried out by sticking on seven different sites of the scalp filter paper disks of 1.9 cm in diameter each containing 0.1 ml of an aqueous solution of 0.5% (w/v) sodium lauryl sulfate.

By this treatment are produced lesions in the scalp as well as disturbances in the regularity of cellular arrangement of scalp surface corneocytes.

(2) After the treatment (1), the closed patches are removed. Samples are applied twice a day, i.e. in the morning (at nine o'clock) and in the evening (at seventeen o'clock), from the following day for two consecutive months for Examples 1–4 and Comparative Example 6 and for one month for Example 15 and Comparative Example 6. The hair is removed if necessary. In order to take into account and avoid site to site variations, the site of application is changed by rotation for each subject. The rate of daily recovery is determined by observing specimens of the stratum corneum, obtained from the scalp surface with an adhesive tape, for cellular arrangement of corneocytes and multi-layer desquamation.

Method of Evaluation (1) The regularity of cellular arrangement of scalp corneocytes is judged by the following five-grade rating:

Score

1. The cell shape is extremely uniform, and the cellular arrangement is extremely regular.
2. The cell shape is uniform, and the cellular arrangement is regular.
3. The cell shape is slightly ununiform, and the cellular arrangement is intermediate.
4. The cell shape is ununiform, and the cellular arrangement is irregular.
5. The cell shape is entirely ununiform, and the cellular arrangement is extremely irregular.

The smaller the numerical rating score, the higher the rate of recovery is in terms of the regularity of cellular arrangement of corneocytes.

(2) The multi-layer desquamation is judged by the following five-grade rating.

Score

1. Small number (less than 5% of all) of cells are multi-layered and densely stained.
2. Small number (5–10% of all) of cells are multi-layered and densely stained.
3. Slightly large number (10–25% of all) of cells are multi-layered and densely stained, and small number of cells are peeling in masses.
4. Large number (25–50% of all) of cells are multi-layered and some of them are peeling in masses.
5. Large number (50% or more of all) of cells are multi-layered and masses of peeling cells are scattered all over.

The smaller the numerical score is, the less the multi-layer desquamation of the stratum corneum is.

A. Test for the recovery of regularity of cellular arrangement of scalp corneocytes and for the improvement in multi-layer desquamation Results

TABLE 2

Results of tests for the recovery of regularity of cellular arrangement of scalp corneocytes and the improvement of multi-layer desquamation

| Sample | Rating of regularity of cellular arrangement of corneocytes | Rating of multi-layer desquamation |
|---|---|---|
| Example | | |
| 1 | 1.7 | 2.0 |
| 2 | 1.5 | 2.0 |
| 3 | 1.4 | 1.6 |
| 4 | 1.3 | 1.4 |
| Comparative Example 1 | 4.1 | 4.5 |

TABLE 13

Results of tests for the recovery of regularity of cellular arrangement of scalp corneocytes

| Sample | Rating score | Standard deviation n = 10 |
|---|---|---|
| Example 15 | 1.3 | ±0.8 |
| Comparative Example 6 | 3.2 | ±0.9*** |

Test of significance: Student's t-Test
Control: Example 15
*** $P < 0.001$

TABLE 14

Results of tests for the improvement of multi-layer desquamation

| Sample | Rating score | Standard deviation n = 10 |
|---|---|---|
| Example 15 | 1.4 | ±0.7 |
| Comparative Example 6 | 3.1 | ±0.6*** |

Test of significance: Student's t-Test
Control: Example 15
*** $P < 0.001$

As is apparent from the test results shown in Tables 2, 13 and 14, all the scalp essences formulated in accordance with Examples 1–4 and 15 gave ratings of 2.0 or less, thus being excellent in the rate of recovery of the regularity of cellular arrangement of corneocytes as well as in the improvement of multi-layer desquamation.

Furthermore, in respect of the rate of recovery of the regularity of cellular arrangement of corneocytes, good results are noted with Examples 1, 2 and 15 where steroid glycoside, triterpenoid glycoside, sphingo glycolipid and steroid hormone are incorporated, as well as with Examples 3 and 4 where resorcin and resorcin and pantethine are added to the ingredients mentioned above, respectively. In contrast, the scalp essences formulated in accordance with Comparative Example 6, where none of steroid glycoside, triterpenoid glycoside and sphingo glycolipid is incorporated, and Comparative Example 1, where none of steroid glycoside, triterpenoid glycoside, sphingo glycolipid and estrone is incorporated, gave ratings of more than 3.0, thus showing low rates of recovery of the regularity of cellular arrangement of corneocytes.

On the other hand, in respect of multi-layer desquamation, it is noted that particularly excellent results are obtained with Examples 3 and 4 where resorcin and resorcin and pantethine are additionally incorporated, respectively, as well as with Example 15 where a larger amount of steroid hormone is used.

B. Visual observation of scalp lesions

Sample

Scalp essence from Example 1

Procedure

Ten healthy male subjects to be tested in their twenties to forties have their hair cut with a hair-cutter and then get their head shaved.

An aqueous solution of 0.5% sodium lauryl sulfate is applied to cause lesions in the scalp. To some of these lesions is applied the scalp essence from Example 1 twice a day from the following day for consecutive seventeen days, while the other lesions are left untreated without any application for spontaneous healing. After seventeen days, specimens of desquamated stratum corneum are prepared from the lesions, both treated and untreated, with an adhesive tape. The state of healing is compared for evaluation by observing the state of the stratum corneum under a microscope. Where the scalp lesions are healed, the stratum corneum is peeled uniformly and thinly, and where there still remain lesions, it is peeled ununiformly and thickly.

Results

In the stratum corneum specimens obtained from the sites where the scalp essence from Example 1 was applied, the phenomenon that the stratum corneum is peeled ununiformly and thickly was found to disappear apparently earlier than in those specimens obtained from the sites where nothing was applied, the effect of recovering scalp lesions thus being shown.

C. Test for hair moisturizing effect

Sample

Scalp essences from Examples 1–4 and Comparative Example 1.

Procedure

Fifty female subjects whose hair is damaged, glossless and dry due to the use of permanent wave fluids are divided at random into five groups of ten each.

After washing the hair with shampoos in ordinary use, a particular sample, predetermined for each subject, is applied and such application is repeated for three weeks.

Sensory evaluation was made by the subjects themselves.

Evaluation criteria

<Hair moisturizing effect>
⊚: Greatly improved
o: Improved
Δ: Little changed Results

TABLE 3

Results of tests for hair moisturizing effect

| Evaluation | Example | | | | Comparative Example |
|---|---|---|---|---|---|
| | 1 | 2 | 3 | 4 | 1 |
| Moisturiz-effect | persons | | | | |
| ⊚ | 8 | 8 | 8 | 9 | 2 |
| o | 2 | 2 | 2 | 1 | 4 |
| Δ | 0 | 0 | 0 | 0 | 4 |

As is apparent from the test results indicated in Table 3 shown above, 8–9 out of 10 subjects were evaluated to be "⊚(greatly improved)" in all the examples. Thus it is shown that the product of the present invention has a significant hair moisturizing effect as compared to that from the Comparative Example.

Examples 5 and 6 and Comparative Example 2

Shampoo is prepared.
Formulation is shogun in Table 4.

TABLE 4

Formulation of Shampoo

| Raw materials | Example | | Comparative Example |
|---|---|---|---|
| | 5 | 6 | 2 |
| Coconut fatty acid diethanolamide | 2.5 | 2.5 | 2.5 |
| ALSCOAP M-3S (Toho Chemical Industry Co., Ltd.)[1] | 10.0 | 10.0 | 10.0 |
| ANON GLM-R (Nippon Oil & Fats Co., Ltd.)[2] | 8.0 | 8.0 | 8.0 |
| BISTAR CAP (Matsumoto Yushi-Seiyaku Co., Ltd.)[3] | 8.0 | 8.0 | 8.0 |
| Polymer JR (Union Carbide)[4] | 0.5 | 0.5 | 0.5 |
| Methyl para-hydroxybenzoate | 0.2 | 0.2 | 0.2 |
| Disodium edetate | 0.1 | 0.1 | 0.1 |
| Perfume | 0.1 | 0.1 | 0.1 |
| 1,3-Butylene glycol | 8.0 | 8.0 | 8.0 |
| Product of Preparation 1 | 1.0 | 1.0 | — |
| Estradiol | 0.1 | 0.1 | — |
| Lanolin | — | — | 1.1 |
| Purified water | 61.5 | 61.2 | 61.5 |
| Ginseng extract | — | 0.1 | — |
| Glycyrrhetinic acid | — | 0.1 | — |
| Allantoin | — | 0.1 | — |

[1] 30% aqueous solution of sodium polyoxyethylene lauryl ether sulfate (3 E.O.)
[2] 2-alkyl-N-carboxymethyl-N-hydroxyethylimidazolinium betaine
[3] 30% aqueous solution of coconut fatty acid amide propyldimethylamino acetic acid betaine
[4] Hydroxyethylcelluiose hydroxypropyltrimethyl ammonium chloride ether Method of Preparation The raw materials in Table 4 are combined together and stirred well at room temperature to give a homogeneous solution.

The shampoos formulated in accordance with Examples 5 and 6 and Comparative Example 2 and the scalp essences formulated in accordance with Examples 2 and 8 and Comparative Example 3 were subjected to the following test for dandruff suppression effect.

D. Test for dandruff suppression effect

Sample

Shampoos from Examples 5 and 6, and Comparative Example 2 and scalp essences from Examples 2 and 8 and Comparative Example 3

Test Method

1) Fifteen subjects who were comparatively dandruffy were divided at random into three groups of five each. The test was conducted for a period of one month and the subjects washed the hair every other day. In washing their hair, they used, for the first two weeks, the shampoo from Comparative Example 2 as a control and immediately thereafter the scalp essence from Comparative Example 1 and, for the subsequent two weeks, the shampoo from Example 5 or 6 or the one from Comparative Example 2 for the purpose of comparison and immediately thereafter the scalp essence from Example 2 or, for the purpose of comparison, the shampoo from Comparative Example 2 and immediately thereafter the scalp essence from scalp essence from Comparative Example 1.

2) Twenty Subjects who were comparatively dandruffy were divided at random into two groups of ten each. The test was conducted for a period of one month and the subjects washed the hair every other day. In washing their hair, they used, for the first weeks, the shampoo from Comparative Example 2 and immediately thereafter the scalp essence from Comparative Example 1 and, for the subsequent two weeks, the shampoo from Example 5 and immediately thereafter the scalp essence from Example 15 or, for the purpose of comparison, the shampoo from Comparative Example 2 and immediately thereafter the scalp essence from Comparative Example 6.

In test methods 1) and 2), collection of dandruff was carried out as follows: The subjects were made to wash the hair over a meshwork basket covered with a non-woven fabric. The non-woven fabric was then air-dried to recover dandruff and hair as a residual solid on the filter. After removal of the hair, the Collected dandruff was dried under reduced pressure and its weight in mg was measured.

Method of Evaluation

Changes in dandruff weights were studied by comparing the mean dry weight of dandruff obtained in the last two hair washings during the use of the control with that obtained in the last two hair washings during two weeks of use of the product of the present invention or the control product.

The % reduction was determined using the following formula:

$$\% \text{ Reduction} = \frac{\text{Dandruff weight after the use of the control} - \text{Dandruff weight after the use of the product from Example or Comparative Example}}{\text{Dandruff weight after the use of the control}} \times 100 \, (\%)$$

Results (i) Shampoo from Example 5

TABLE 5

Results of Dandruff Suppression Test (Example 5)

| Subject | Dandruff weight (mg) | | Reduction (%) |
|---|---|---|---|
| | Control | Example 5 | |
| 1 | 36.2 | 17.3 | 52.2 |
| 2 | 33.4 | 16.2 | 51.5 |
| 3 | 26.0 | 13.1 | 49.6 |
| 4 | 51.2 | 25.3 | 50.6 |
| 5 | 56.7 | 32.2 | 43.2 |
| Mean | | | 49.4 |

As is apparent from Table 5, a significant dandruff suppression effect was observed in all the five subjects, the mean percent reduction being 49.4%.

(ii) Shampoo from Example 6

TABLE 6

Results of Dandruff Suppression Test (Example 6)

| Subject | Control | Example 5 | Reduction (%) |
|---|---|---|---|
| 1 | 34.6 | 13.8 | 60.1 |
| 2 | 31.4 | 13.5 | 57.0 |
| 3 | 23.0 | 11.0 | 52.2 |
| 4 | 52.1 | 25.3 | 51.4 |
| 5 | 58.5 | 26.1 | 55.4 |
| Mean | | | 55.2 |

As is apparent from Table 6, a significant dandruff suppression effect was observed in all the five subjects, the mean percent reduction being 55.2%.

(iii) Comparative Example 2

TABLE 7

Results of Dandruff Suppression Test (Comparative Example 2)

| Subject | Dandruff weight (mg) | | Reduction (%) |
|---|---|---|---|
| | Control | Comparative Example 2 | |
| 1 | 35.5 | 22.0 | 38.0 |
| 2 | 31.2 | 21.4 | 31.4 |
| 3 | 25.0 | 16.2 | 35.1 |
| 4 | 47.0 | 33.4 | 28.9 |
| 5 | 59.1 | 40.0 | 32.3 |
| | Mean | | 33.1 |

As is apparent from Table 7, Comparative Example 2 gave the mean percent dandruff reduction of 33.1% thus showing a poorer dandruff reduction effect than in Examples 5 and 6.

(iv) Scalp essences from Example 15 and Comparative Example 6

TABLE 15

| Sample | Mean by weight of dandruff (mg) | |
|---|---|---|
| | Rating score $\bar{X} \pm S.D.$ | n = 10 |
| Example 15 | 20.5 ± 9.4 | |

TABLE 15-continued

| Sample | Mean by weight of dandruff (mg) Rating score X̄ ± S.D. | n = 10 |
|---|---|---|
| Comparative Example 6 | 34.2 ± 12.4 | * |

Test of significance: Student's t-Test
Control: Example 15
*P < 0.05

As is apparent from Table 15, the scalp essence from Example 15 is observed to give a significant dandruff suppression effect over the one from Comparative Example 6.

Example 7

Tonic is prepared.

Formulation is shogun in Table 8.

TABLE 8

| Formulation of Tonic | |
|---|---|
| Raw materials | Example 7 |
| (1) Ethanol | 50 |
| l-Menthol | 0.2 |
| Perfume | 0.2 |
| Polyoxyethylene hydrogenated castor oil (50 E.O.) | 0.5 |
| Product of Preparation 1 | 0.5 |

TABLE 8-continued

| Formulation of Tonic | |
|---|---|
| Raw materials | Example 7 |
| Cortisone | 0.02 |
| dl-α-Tocopherol acetate | 0.5 |
| (2) Citric acid | 0.13 |
| Sodium citrate | 0.05 |
| Purified water | 46.9 |
| Placentas extract | 1.0 |

Method of Preparation

The raw materials indicated in (1) in Table 8 were mixed with and dissolved in those indicated in (2) in Table 8 shown above with stirring to prepare a tonic.

[External Skin Preparation]

Examples 8–14 and 16 and Comparative Examples 3–5 and 7–10 relate to external skin preparation.

Example 8 and Comparative Examples 3–5 relate to oil-in-water type cream.

Formulation is shown in Table 9.

TABLE 9

| | Formulation of Oil-in-Water Cream | | | |
|---|---|---|---|---|
| Raw materials | Example 8 | Comparative Example 3 | Comparative Example 4 | Comparative Example 5 |
| (1) Squalane | 13 | 13 | 13 | 13 |
| Jojoba oil | 3 | 3 | 3 | 3 |
| Silicone oil | 2 | 2 | 2 | 2 |
| Behenic acid | 2 | 2 | 2 | 2 |
| Synthetic spermaceti | 3 | 3 | 3 | 3 |
| Polyoxyethelene sorbitan monostearate (20 E.O.) | 1.5 | 1.5 | 1.5 | 1.5 |
| Lipophilic glycerin monostearate | 1.2 | 1.2 | 1.2 | 1.2 |
| Product of Preparation 1 | 3 | 3 | 0 | 0 |
| (2) 1,3-Butylene glycol | 5 | 5 | 5 | 5 |
| Glycerin | 3 | 3 | 3 | 3 |
| Purified water | 62.99 | 63 | 65.99 | 66 |
| Methyl para-hydroxybenzoate | 0.1 | 0.1 | 0.1 | 0.1 |
| (3) Estrone | 0.01 | 0 | 0.01 | 0 |
| Perfume | 0.2 | 0.2 | 0.2 | 0.2 |

Method of Preparation

The raw materials indicated in (1) in Table 9 and those indicated in (2) in Table 9 shown above are separately dissolved by heating them at 80° C. A part of the solution from (2) is slowly added with stirring to the solution from (1) and after reversal emulsification the remainder of the solution from (2) is added. The mixture is cooled down to 40° C. and after addition of the raw materials indicated in (3) further down to 30° C.

Example 16 and Comparative Examples 7–10 relate to water-in-oil type cream.

Formulation is shown in Table 16.

TABLE 16

| | Raw materials | Example 16 | Comparative Example 7 | Comparative Example 8 | Comparative Example 9 | Comparative Example 10 |
|---|---|---|---|---|---|---|
| | Formulation of Water-in-Oil Cream | | | | | |
| (1) | Bees wax | 5 | 5 | 5 | 5 | 5 |
| | Micro-crystalline wax | 6 | 6 | 6 | 6 | 6 |
| | Liquid petrolatum | 15 | 15 | 15 | 15 | 15 |
| | Pyroglutamic acid monooleate | 4 | 4 | 4 | 4 | 4 |
| | Butyl para-hydroxy benzoate | 0.1 | 0.1 | 0.1 | 0.1 | 0.1 |
| | Steroid glycoside and triterpenoid glycoside | 8 | 8 | 8 | 0 | 0 |
| | Sphingo glycolipid | 2 | 2 | 0 | 2 | 0 |
| (2) | 4-O—α-D-gluco-pyranal-sorbitol | 6 | 6 | 6 | 6 | 6 |
| | Purified water | 53.796 | 53.7 | 55.696 | 61.696 | 63.696 |
| (3) | Estrone | 0.004 | 0 | 0.004 | 0.004 | 0.004 |
| | Dipotassium glycyrrhetinate | 0 | 0.1 | 0 | 0 | 0 |
| | Allantoin | 0 | 0 | 0.1 | 0 | 0 |
| | Vitamin E | 0 | 0 | 0 | 0.1 | 0 |
| | Sodium hyaluronate | 0 | 0 | 0 | 0 | 0.1 |
| | Perfume | 0.1 | 0.1 | 0.1 | 0.1 | 0.1 |

Results of the following tests A, B, B', C and C' will be shown below which were carried out with the external skin preparation in accordance with the present invention:

A: Test for the normalization and retardation of stratum corneum turnover;

B: Test for the recovery of the regularity of cellular arrangement of corneocytes;

B': Test for the improvement in multi-layer desquamation;

C: Visual observation for skin-roughening improvement effect; and

C': Test for water content improvement effect by measurement of skin surface conductance.

A. Test for the normalization and retardation of stratum corneum turnover.

Sample

Oil-in-water type cream formulated in accordance with Example 8 and Comparative Examples 3–5.

Procedure

The dansyl chloride method is employed. This method involves binding dansyl chloride, which emits fluorescence when irradiated with ultra violet, to corneocytes and determining the stratum corneum turnover time from the rate of attenuation of the fluorescence. Details of the dansyl chloride method are described in G. L. Grove & A. M. Kligman, Stratum Corneum, p.191 (1983) (Springer-Verlag Berlin Heidelberg New York).

Results

The results are as shown in FIGS. 1–4.

In FIG. 1, the external skin preparation from Comparative Example 3, where steroid glycoside, triterpenoid glycoside and sphingo glycolipid are contained but steroid hormone is not contained, is indicated by —o—, while the one from Comparative Example 5, where none of steroid glycoside, triterpenoid glycoside, sphingo glycolipid and steroid hormone is contained, is indicated by —◌—. As is apparent from FIG. 1, the turnover, which normally attenuates linearly, shows an exponential attenuation in Comparative Example 5, whereas it is found in Comparative Example 3 to show a linear attenuation and therefore to be normalized. In the case of Comparative Example, however, little function of retarding the stratum corneum turnover is observed.

Figure 2:
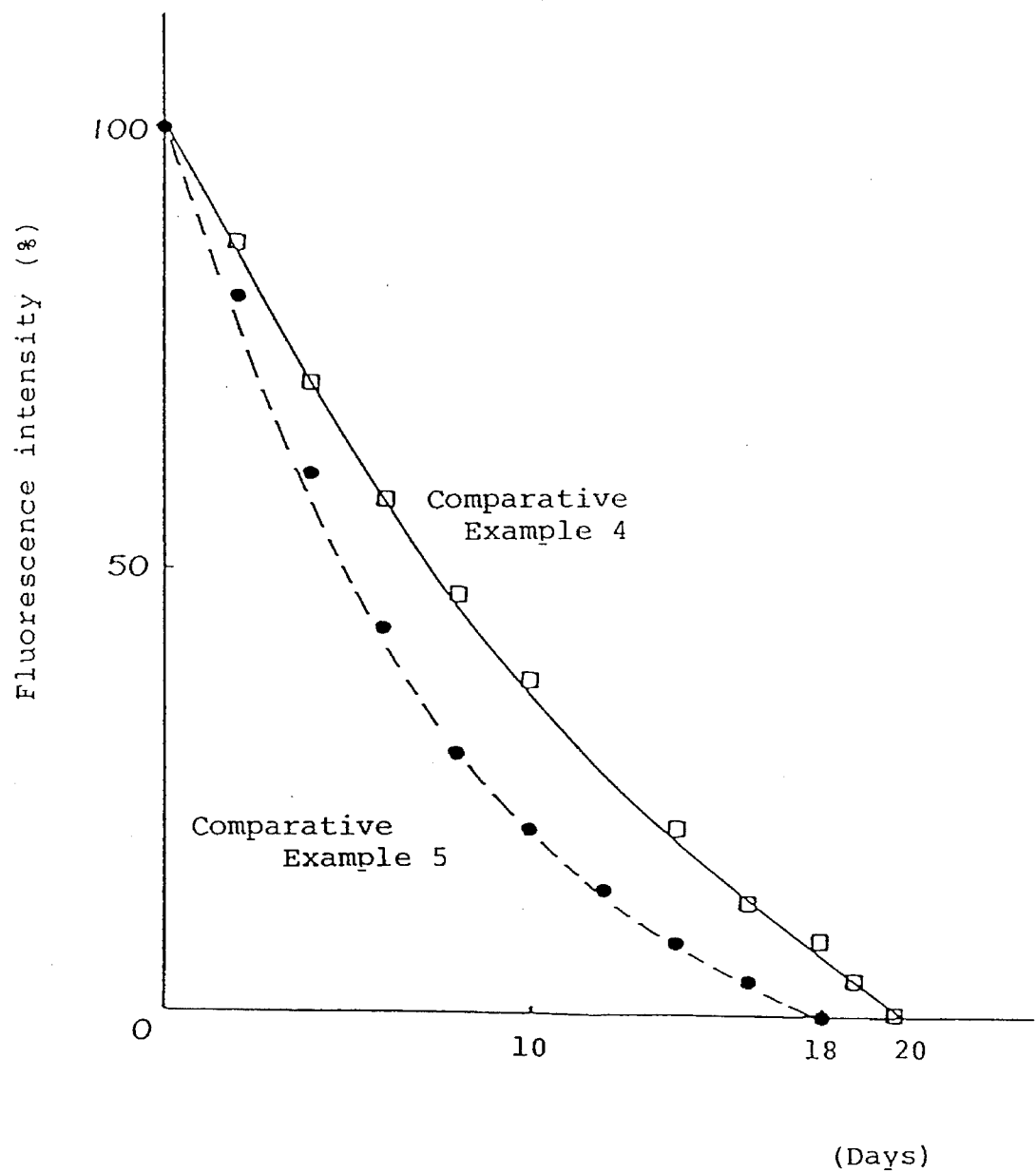

As shown from FIG. 2, the external skin preparation from Comparative Example 4, where steroid hormone is contained but none of steroid glycoside, triterpenoid glycoside and sphingo glycolipid is contained, is found to have the function of retarding the turnover of irregularized stratum corneum, but to show an exponential attenuation, i.e. little function of normalizing the stratum corneum turnover.

As shown in FIG. 3, the external skin preparation from Example 8, where steroid glycoside, triterpenoid glycoside, sphingo glycolipid and steroid hormone are contained, is found to have the function of normalizing and retarding the stratum corneum turnover.

As shown in FIG. 4, the external skin preparations from Comparative Example 7, where none of steroid glycoside, triterpenoid glycoside and steroid hormone is contained, and from Comparative Example 8, where steroid glycoside and triterpenoid are contained but sphingo glycolipid is not contained, are found to have the function of normalizing, but little function of retarding, the stratum corneum turnover. The external skin preparations from Comparative Example 9, where sphingo glycolipid and steroid hormone and contained but none of steroid glycoside and tritepenoid glycoside is contained, and from Comparative Example 10, where steroid hormone is contained but none of steroid glycoside, triterpenoid glycoside and sphingo glycolipid is contained, are found to have the function of retarding the turnover of irregularized stratum corneum, but to show an exponential attenuation, i.e. little function of normalizing the stratum corneum turnover. In contrast, the external skin preparation from Example 16, where steroid glycoside, triterpenoid glycoside, sphingo glycolipid and steroid hormone are contained, is found to have the function of normalizing and retarding the stratum corneum turnover.

These effects of normalizing and retarding the stratum corneum turnover bring about favorable effects on the skin, such as improvement of skin-roughening or the like state. Furthermore, these effects of improvement deserve special mention as outstanding advantageous features which have never been achieved by the prior art, since they do not merely improve the surface state of the skin but they drastically better the skin as a whole from inside the skin.

B. Test for the recovery of the regularity of cellular arrangement of corneocytes.

Samples

Oil-in-water type cream formulated in accordance with Example 8 and Comparative Examples 3–5.

Procedure (1) A twenty four-hour closed patch test is carried out by sticking on six different sites of the inside skin of the human upper arm filter paper discs of 1.9 cm in diameter each containing 0.1 ml of an aqueous solution of 0.5% (w/v) sodium lauryl sulfate.

There were used twenty healthy male subjects in their twenties to forties.

By this treatment is produced a rough state of the skin, which represents the irregulation of cellular arrangement of corneocyte.

(2) After the treatment (1), the closed patches are removed. Samples are applied twice a day, i.e. in the morning (at nine o'clock) and in the evening (at seventeen o'clock), from the following day for consecutive two months. In order to take into account and avoid site to site variations, the site of application is changed by rotation for each subject. The rate of daily recovery is determined by observing specimens of the stratum corneum, stripped off from the skin surface with an adhesive type, for the regularity of cellular arrangement of corneocytes.

Samples

Water-in-oil type cream formulated in accordance with Example 16 and Comparative Examples 7–10.

Procedure (1) A twenty four-hour closed patch test is carried out by sticking on six different sites of the inside skin of the human upper arm filter paper discs of 1.9 cm in diameter each containing 0. 1 ml of an aqueous solution of 0.5% (w/v) sodium lauryl sulfate.

There were used ten healthy male subjects in their twenties to forties.

By this treatment is produced a rough state of the skin, which represents the irregulation of cellular arrangement of corneocyte.

(2) After the treatment (1), the closed patches are removed. Samples are applied twice a day, i.e. in the morning (at nine o'clock) and in the evening (at seventeen o'clock), from the following day for one consecutive month. In order to take into account and avoid site to site variations, the site of application is changed by rotation for each subject. The rate of daily recovery is determined by observing specimens of the stratum corneum, stripped off from the skin surface with an adhesive type, for the regularity of cellular arrangement of corneocytes.

The regularity of cellular arrangement of corneocytes is judged by the following five-grade rating:

Score

1. The cell shape is extremely uniform and the cellular arrangement is extremely regular.
2. The cell shape is extremely uniform and the cellular arrangement is regular.
3. The cell shape is slightly ununiform and the cellular arrangement is intermediate.
4. The cell shape is ununiform and the cellular arrangement is irregular.
5. The cell shape is entirely ununiform and the cellular arrangement is extremely irregular.

Results

TABLE 10

| | Rating score | Standard deviation n = 20 |
| --- | --- | --- |
| Example 8 | 1.2 | ±0.7 |
| Comparative Example 3 | 2.3 | ±1.1 |
| Comparative Example 4 | 3.5 | ±0.9 |
| Comparative Example 5 | 3.9 | ±1.0 |
| Control with nothing applied | 4.4 | ±1.0 |

TABLE 17

| Samples | Rating score | Standard deviation n = 10 |
| --- | --- | --- |
| Example 16 | 1.5 | ±0.5 |
| Comparative Example 7 | 3.5 | ±1.2*** |
| Comparative Example 8 | 2.4 | ±0.7** |
| Comparative Example 9 | 3.0 | ±0.6*** |
| Comparative Example 10 | 3.2 | ±0.6*** |
| Control with nothing applied | 3.8 | ±1.0*** |

Test of significance: Student's t-Test
Control: Example 16
**P < 0.01
***P < 0.001

The results are shown in Tables 10 and 17 above. The rating scores indicated in Tables 10 and 17 are those determined by statistical processing of recovering effect ratings, obtained upon two months of application of tested samples, on the basis of the five-grade evaluation results in respect of the regularity of cellular arrangement of corneocytes. The smaller the numerical rating score is, the higher the rate of recovery is in terms of the regularity of cellular arrangement of corneocytes.

From these test results, it is shown that Example 8 gives a higher incidence of being rated as first than any of Comparative Examples 3–5 and also that its effect of recovery is significantly high statistically. A significant difference was found between Comparative Examples 3 and 4, but neither between Comparative Examples 4 and 5 and a control with nothing applied nor between Comparative Example 5 and the control. As is apparent from Table 17, the Example 16 gives a smaller rating score, showing a statistically significant recovery of the regularity of cellular arrangement of corneocytes as compared with Comparative Examples 7–10 and the control.

It was demonstrated from these results that the effect of regularizing the cellular arrangement of corneocytes achieved when steroid glycoside and/or triterpenoid glycoside and sphingo glycolipid are contained but no steroid hormone is synergetically increased by additionally incorporating steroid hormone.

B'. Test for the improvement in multi-layer desquamation

Samples

Water-in-oil type cream formulated in accordance with Example 16 and Comparative Examples 7–10.

Procedure (1) A twenty four-hour closed patch test is carried out by sticking on six different sites of the flexor aspect of the human forearm filter paper disks of 1.9 cm in diameter each containing 0.1 ml of an aqueous solution of 0.5% (w/v) sodium lauryl sulfate.

There were us ed ten healthy male subjects in their twenties to forties.

By this treatment is produced a rough state of the skin, which represents the irregulation of cellular arrangement of corneocytes.

(2) After the treatment (1), the closed patches are removed. Samples are applied twice a day, i.e. in the morning (at nine o'clock) and in the evening (at seventeen o'clock), from the following day for consecutive one month. In order to take into account and avoid site to site variations, the site of application is changed by rotation for each subject. The rate of daily recovery is determined by observing specimens of the stratum corneum, obtained from the skin surface with an adhesive tape, for multi-layer desquamation.

Method of evaluation

The multi-layer desquamation is judged by the following five-grade rating

Score

1. Small number (less than 5% of all) of cells are multi-layered and densely stained.
2. Small number (5–10% of all) of cells are multi-layered and densely stained.
3. Slightly large number (10–25% of all) of cells are multi-layered and densely stained, and small number of cells are peeling in masses.
4. Large number (25–50% of all) of cells are multi-layered and some of them are peeling in masses.
5. Large number (50% or more of all) of cells are multi-layered and masses of peeling cells are scattered all over.

The smaller the numerical score is, the less the multi-layer desquamation of the stratum corneum is.

Results

TABLE 18

| Samples | Rating score | Standard deviation n = 10 |
|---|---|---|
| Example 16 | 1.6 | ±0.6 |
| Comparative Example 7 | 3.2 | ±0.9*** |
| Comparative Example 8 | 2.6 | ±0.3** |
| Comparative Example 9 | 2.9 | ±0.5*** |
| Comparative Example 10 | 3.0 | ±0.4*** |
| Control with nothing applied | 3.6 | ±0.9*** |

Test of significance: Student's t-Test
Control: Example 16
**$P < 0.01$
***$P < 0.001$ As is shown in Table 18, the Example 16 is found to give a statistically significant reduction, thus an excellent improvement, in the multi-layer desquamation of corneocytes because of its showing a smaller rating score than in Comparative Examples 7–10 and the control.

C. Visual observation for water content improvement effect.

Sample

Oil-in-water type cream from Example 8

Procedure

An aqueous solution of 0.5% sodium lauryl sulfate was applied to the inside normal skin of the human upper arm to cause lesions there. To some of such lesions is applied the external skin preparation from Example 8 twice a day from the following day for seventeen consecutive days, while the other lesions are left untreated without any application for spontaneous healing. After seventeen days, the skin-roughening improvement effect on lesions, both treated and untreated, is evaluated by observing the state of the stratum corneum under a microscope with specimens of desquamated stratum corneum peeled off from the skin with an adhesive tape. Where the skin is not roughened, the stratum corneum is peeled uniformly and thinly, and where the skin is roughened, it is peeled ununiformly and thickly.

In the stratum corneum specimens obtained from the sites where the topical agent from Example 8 was applied, the phenomenon that the stratum corneum is peeled ununiformly and thickly was found to disappear apparently earlier than in those specimens obtained from the sites where nothing was applied, the skin-roughening improvement effect thus being shown.

C'. Test for water content improvement effect by measurement of skin surface conductance Sample Water-in-oil type cream formulated in accordance with Example 16 and Comparative Examples 7–10.

Procedure

Method for the measurement of skin surface conductance:

Fifty female subjects who were subject to skin-roughening were divided into five groups of ten subjects each. 5 μg/cm$^2$ of sample predetermined for each group was applied, once a day, to the flexor side of the human forearm for one month. After the subjects were allowed to stand still for 40 minutes in a room kept at 20° C. and a humidity of 50%, the skin surface conductance was measured using a SKICON-200 (supplied by IBS).

The greater the value of conductance is, the higher the water content is. The roughened skin is known to have a relatively low water content as well as a relatively small value of conductance.

Results

TABLE 19

Measurement of skin surface conductance (μv)

| Samples | Rating score $\bar{X} \pm$ S.D. | n = 10 |
|---|---|---|
| Example 16 | 19.2 ± 5.2 | |
| Comparative Example 7 | 15.0 ± 3.5 | * |
| Comparative Example 8 | 12.1 ± 4.7 | ** |
| Comparative Example 9 | 13.8 ± 4.0 | * |
| Comparative Example 10 | 10.3 ± 3.5 | *** |
| Control with nothing applied | 8.5 ± 5.6 | *** |

Test of significance: Student's t-Test
Control: Example 16
*P < 0.05
**P < 0.01
***P < 0.001

As is apparent from Table 19, the sample in accordance with the present invention from Example 16 gives a statistically significant increase in skin surface conductance comparing with the samples from Comparative Examples 7–10 and the control, thus showing an excellent improvement effect on the water content of the skin.

Examples 9–13

Water-in-Oil type cream is prepared.
Formulation is shown in Table 11.

TABLE 11

Formulation of water-in-oil cream

| Raw materials | Example 9 | Example 10 | Example 11 | Example 12 | Example 13 |
|---|---|---|---|---|---|
| (1) Bees wax | 5 | 5 | 5 | 5 | 5 |
| Microcrystalline wax | 6 | 6 | 6 | 6 | 6 |
| Liquid petrolatum | 15 | 15 | 15 | 15 | 15 |
| Pyroglutamic acid monooleate | 4 | 4 | 4 | 4 | 4 |
| Butyl para-hydroxybenzoate | 0.1 | 0.1 | 0.1 | 0.1 | 0.1 |
| Steroid glycoside and triterpenoid glycoside | 8 | 8 | 8 | 8 | 8 |
| Sphingo glycolipid | 2 | 2 | 2 | 2 | 2 |
| (2) 4-O—α-D-glucopyranal-sorbitol | 6 | 6 | 6 | 6 | 6 |
| Purified water | 53.79 | 53.69 | 53.69 | 53.69 | 53.69 |
| (3) Hydrocortisone acetate | 0.01 | 0.01 | 0.01 | 0.01 | 0.01 |
| Dipotassium glycyrrhetinate | 0 | 0.1 | 0 | 0 | 0 |
| Allantoin | 0 | 0 | 0.1 | 0 | 0 |
| Vitamin E | 0 | 0 | 0 | 0.1 | 0 |
| Sodium hyaluronate | 0 | 0 | 0 | 0 | 0.1 |
| Perfume | 0.1 | 0.1 | 0.1 | 0.1 | 0.1 |

Method of Preparation

The raw materials indicated in (1) in Table 11 are homogeneously dissolved at 80° C., and to the resultant solution are added the ingredients indicated in (2) which had been homogeneously dissolved at 80° C. to form an emulsion. To the emulsion are added, while cooling, the raw materials indicated in (3) at 40° C., and the resultant mixture is cooled further down to 30° C.

Example 14 Ointment

| Formulation | | |
|---|---|---|
| (1) | Liquid paraffin | 23.9 |
| | Vaseline | 46.0 |
| | Polyoxyethylenesorbitan monostearate (20 E.O.) | 4.0 |
| | Sorbitan monostearate | 2.0 |
| | Steroid glycoside | 0.8 |
| | Sphingo glycolipid | 0.2 |
| | Bees wax | 3.0 |
| | Cetanol | 1.0 |
| (2) | Glycerin | 10.0 |
| | Purified water | 5.0 |
| (3) | Estrone | 0.01 |
| | Allantoin | 0.09 |
| | Purified water | 4.0 |

Method of Preparation

The raw materials (1) and (2) in the formulation shown above are separately heated at 80° C. and then homogeneously mixed by slowly adding (1) to (2) with stirring. The resultant mixture is cooled down to 40° C. and (3) is added.

Thus, by using the external skin preparations in accordance with the present invention on the one hand, the turnover of the stratum corneum of the skin can be normalized and retarded with the result that the regularity of cellular arrangement of corneocytes can be recovered and skin-roughening improved.

By using the scalp moisturizer in accordance with the present invention on the other hand, the turnover of the stratum corneum of the scalp can be normalized and this normalization effect leads to the improvement of multi-layer desquamation as well as to the recovery of cellular arrangement of corneocytes with the result that dandruff production in the scalp can be suppressed and the scalp moisturized.

What is claimed is:

1. A scalp moisturizer preparation, comprising (a) a steroid glycoside and/or a triterpenoid glycoside, (b) a sphingo glycolipid and (c) a follicular hormone and/or an adrenocortical hormone, the content of (a) and (b) being 0.01–10% by weight of the total, the (a)/(b) ratio by weight being 85/15–30/70 and (c) being incorporated in effective amounts of not more than 0.1% by weight of the total, wherein said scalp moisturizer preparation which is effective in suppressing dandruff and providing the hair with moisture through the normalization and retardation of the turnover of the scalp stratum corneum.

2. The scalp moisturizer as claimed in claim 1, further comprising one or more sebum secretion inhibitors and/or antibacterial agents with potent antibacterial activity against the microbe *Pityrosporum ovale*.

3. An external skin preparation, comprising (a) a steroid glycoside and/or a triterpenoid glycoside, (b) a sphingo glycolipid and (c) a follicular hormone and/or an adrenocortical hormone, the content of (a) and (b) being 0.01–10% by weight of the total, the (a)/(b) ratio by weight being 85/15–30/70 and (c) being incorporated in effective amounts of not more than 0.1% by weight of the total, wherein said external skin preparation is effective in promoting the recovery of the regularity of the cellular arrangement of corneocytes through the normalization and retardation of the turnover of the stratum corneum.

4. The external skin preparation as claimed in claim 3, further comprising at least one member selected from the group consisting of an anti-inflammatory agent, a cell activator, a peroxidized lipid formation inhibitor, and a humectant, the cell activator being selected from the group consisting of allantoin, and an extract of Japanese Angelica, rosemary and placentas.

5. The external skin preparation as claimed in claims 3 or 4, wherein at least one member selected from the group consisting of allantoin, and an extract of Japanese Angelica, rosemary or placentas is additionally incorporated in an effective amount for activation of dermal cells.

6. The scalp moisturizer as claimed in claim 1, wherein the content of (a) and (b) is in the range from 0.5 to 2.0% by weight of the total.

7. The external skin preparation as claimed in claim 3, wherein the content of (a) and (b) is in the range from 0.5 to 2.0% by weight of the total.

8. The preparation of claims 1 or 3, wherein said steroid glycoside is a member selected from the group consisting of campesterol glycoside, stigmasterol glycoside, B-sitosterol glycoside, cholesterol glycoside, stigmasterol glycoside and avenasterol glycoside.

9. The preparation of claims 1 or 3, wherein said triterpenoid glycoside is a member selected from the group consisting of cycloartenol glycoside, 24-methylenecycloartenol glycoside, cycloartanol glycoside, cyclobranol glycoside, glycyrrhizin and ginsenoside.

10. The preparation of claims 1 or 3, wherein said sphingo glycolipid contains a dihydrosphingosine, sphingosine, phytosphingosine, or dehydrophytosphingosine skeleton.

11. The preparation of claims 1 or 3, wherein said sphingo glycolipid is a member selected from the group consisting of a monohexosylceramide, a sphingoplasmalogen, a monohexosylceramide fatty acid ester, a dihexosylceramide, a trihexosylceramide, a galactosyl-ceramide sulfate, a dihexosyl-ceramide sulfate, a globoside, N-acetylgalactosamine-(1→4) D-galactosyl (1→4) D-glucosyl (1→) ceramide, D-galactosyl (1→3) N-acetylgalactosamine (1→4) D-galactosyl (1→4) glucosyl (1→) ceramide, D-galactosyl (1→3) D-galactosyl (1→3) N-acetylglucosamine (1→3) D-galactosyl (1→4) D-glucosyl (1→) ceramide, a hematoside, and a ganglioside containing both sialic acid and hexosamine in addition to neutral glucide.

12. The preparation of claims 1 or 3, wherein the (a)/(b) ratio by weight is 60/40–85/15.

13. The preparation of claims 1 or 3, wherein component (c) is present in an amount in the range from 0,001–0.1% by weight of the total composition.

14. The preparation of claim 11, wherein said monohexosylceramide fatty acid ester is a member selected from the group consisting of galactosylceramide fatty acid ester and glycosylceramide fatty acid ester; said dihexosylceramide is a member selected from the group consisting of D-galactosyl(1→4)D-glycosyl (1→) ceramide and D-galactosyl (1→4) D-galactosyl (1→) ceramide; said trihexosylceramide is D-galactosyl (1→4) D-galactosyl (1→4)D-glucosyl (1→) ceramide; said globoside is N-acetylgalactosamine (1→3) D-galactosyl (1→4) galactosyl (1→4) D-glucosyl (1→) ceramide; and said hematoside is a member selected from the group consisting of N-acetylneuraminic acid (2→3) D-galactosyl (1→4) D-glucosyl (1→)ceramide and N-acetylneuraminic acid (2→3) D-galactosyl (1→)ceramide.

* * * * *